US008691835B2

(12) United States Patent
Miller

(10) Patent No.: US 8,691,835 B2
(45) Date of Patent: *Apr. 8, 2014

(54) 4 AMINOPYRIDINE AND A PHARMACEUTICAL COMPOSITION FOR TREATMENT OF NEURONAL DISORDERS

(76) Inventor: Landon C. G. Miller, Tuscaloosa, AL (US)

( * ) Notice: Subject to any disclaimer, the term of this patent is extended or adjusted under 35 U.S.C. 154(b) by 516 days.

This patent is subject to a terminal disclaimer.

(21) Appl. No.: 13/012,688

(22) Filed: Jan. 24, 2011

(65) Prior Publication Data

US 2011/0224266 A1    Sep. 15, 2011

Related U.S. Application Data

(63) Continuation-in-part of application No. 11/023,241, filed on Dec. 27, 2004, now Pat. No. 7,884,079.

(51) Int. Cl.
*A01N 43/40*    (2006.01)
*A61K 31/435*    (2006.01)

(52) U.S. Cl.
USPC .......................................................... 514/277

(58) Field of Classification Search
None
See application file for complete search history.

(56) References Cited

U.S. PATENT DOCUMENTS

| | | | |
|---|---|---|---|
| 5,580,580 | A | 12/1996 | Masterson et al. |
| 6,008,243 | A | 12/1999 | Bender et al. |
| 6,388,054 | B1 | 5/2002 | Stewart et al. |
| 7,884,079 | B2 | 2/2011 | Miller |

FOREIGN PATENT DOCUMENTS

| | | |
|---|---|---|
| CZ | 231250 | 7/1983 |
| WO | WO-9107963 A1 | 6/1991 |
| WO | WO-9639384 A1 | 12/1996 |
| WO | WO-0104119 A1 | 1/2001 |
| WO | WO-03045878 A2 | 6/2003 |

OTHER PUBLICATIONS

Shin et al., Bull. Chem. Soc. Jpn., 1993, 66, 2048-2053.*
Aronson. Potassium channels in nervous tissue. Biochem. Pharmacol. 43(1)11-4 (Jan. 9, 1992) (abstract).
Grijalva et al. Efficacy and safety of 4-aminopyridine in patients with long-term spinal cord injury: a randomized, double . . . Pharmacotherapy 23(7):823-34 (Jul. 2003) (abstract).
Bever, The current status of studies of aminopyridines in patients with multiple sclerosis. Ann. Neurol. 36 Suppl:S118-21 (1994) (abstract).
Young. Diaminopyridine Treatment of Neurological Disorders from http://carecure.rutgers.edu/spinewire/Articles/DAP/DAP.htm (Mar. 17, 2003).
Release of Transmitters from Synaptic Vesicles from http://www.ncbi.nlm.nih.gov/entrez . . . (2001).
Schechter. The Potassium Channel Blockers 4-Aminopyridine and Tetraethylammonium Increase the Spontaneous Basal Release . . . J. Pharmacol. Exp. Ther. 282(1):262-270 (1997).
Poduslo et al. Macromolecular permeability across the blood-nerve and blood-brain barriers. Proc. Natl. Acad. Sci. USA 91:5705-5709 (Jun. 1994).
Lee et al. Drug Transporters in the Central Nervous System: Brain Barriers and Brain Parenchyma Considerations. Pharmacol. Rev. 53(4):569-596 (2001).
Banks et al. Extent and Direction of Ghrelin Transport Across the Blood-Brain Barrier Is Determined by Its Unique Primary . . . J. Pharmacol. Exp. Ther. 302(2):822-827 (2002).
Pan et al. Polypeptide delivery across the blood-brain barrier. Curr. Drug Targets CNS Nerol. Disord. 3(2):131-6 (Apr. 2004) (abstract).
Pardridge. Blood-brain barrier carrier-mediated transport and brain metabolism of amino acids. Neurochem. Res. 23(5):635-44 (May 1998) (abstract).
Smith. Transport of Glutamate and Other Amino Acids at the Blood-Brain Barrier. J. Nutr. 130:1016S-1022S (2000).
Halter et al. Intrathecal administration of 4-aminopyridine in chronic spinal injured patients. Spinal Cord 38(12):728-32 (Dec. 2000) (abstract).
Hayes et al. Pharmacokinetic studies of single and multiple oral doses of fampridine-SR (sustained-release . . . Clin. Neuropharmacol. 26(4):185-92 (Jul.-Aug. 2003) (abstract).
Segal et al. Absorption characteristics of sustained-release 4-aminopyridine (fampridine SR) in patients with chronic spinal cord . . . J. Clin. Pharmacol. 40:402-409 (2000).
Grimaldi et al. Mobilization of Calcium from Intracellular Stores, Potentiation of Neurotransmitter-Induced Calcium Transients . . . J. Neurosci. 21(9):3135-3143 (May 1, 2001).
Lin et al. Enhanced cell-permeant Cre protein for site-specific recombination in cultured cells. BMC Biotechnology 4:25 (2004).
Altman et al., "Synthesis of pyridine derivatives of L-phenylalanine as antisickling reagents," J. Med. Chem., 1084, 27, 596-600.
Molard et al., "Novel synthetic receptors based on para-aminopyridine ligands coupled to p-tert-butylcalix[4]arene via amino-acid spacers," Tet. Let., 2001, 42, 4799-4802.
Guo et al., "Chiroptical Transcription of Helica Invormation through Supramolecular Harmonization with Dynamic Helices," J. Am. Chem. Soc., 2004, 126, 717-7 and supplementary materals.

(Continued)

*Primary Examiner* — Marcela M Cordero Garcia
*Assistant Examiner* — Kaipeen Yang
(74) *Attorney, Agent, or Firm* — Blue Filament Law PLLC; Avery N. Goldstein

(57) ABSTRACT

A composition is provided having the formula

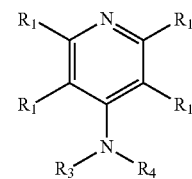

where $R_1$ in each occurrence is independently H or a $C_1$-$C_4$ hydrocarbon; $R_3$ is H, and $R_4$ is a moiety capable of crossing the blood brain barrier selected from the group consisting of: an amino acid, a peptide, transferrin, gluconate, lactate, citrate, malate, fumarate, benzoate, salicylate, pyruvate and propionate. The composition includes 4-aminopyridine and a transporter species which allows for improved transport of the aminopyridine across the blood brain barrier thereby reducing systemic side effects of aminopyridine administration.

3 Claims, No Drawings

(56) References Cited

OTHER PUBLICATIONS

Gau et al., "One-pot optical resolution of oligopeptide helices through artificial peptide bundling," Ang. Chem., 2004, 43, 4915-18.

Ogretir et al., "Quantum chemical studies on acidity-basicity behaviors of some substituted pyridine derivatives," J. Mol. Truct.: THEOCHEM, 2006, 759, 73-8.

Dolzhenko et al., "Substituted amides and hydrazides of dicarboxylic acids. Part 11. Synthesis and pharmacological activity of a series of pyridylamides of dicarboxylic acids", Pharmaceutical Chemistry Journal (Translation of Khimiko-Farmatsevticheskii Zhurnal) (2002), 36(3), 125-127.

File CASREACT on STN, Entered into STN 2001. A Number 64:84452 Casreact, Buzas et al. Reactivity of carbodimides. Application to the acylation of 2-,3-, 4-aminopyridines. Comptes Rendus des Seances de l'Academie des Scineces, Serie C: Sciences Chimiques (1966), 262(8), 658-61. Abstract Only.

Pardridge, "Why is the global CNS pharmaceutical market so underpenetrated?" Drug Disc. Today, 2002, 7, 5-7.

Anand et al., "Current prodrug strategies via membrane transporters/receptors." Exp. Op., 2002, 2, 608-20.

Yoshikawa et al., "A novel chemical delivery system for brain targeting." Adv. Drug Del., 1999, 36, 255-75.

Sakaeda et al., "Conjugation with L-Glutamate for in vivo brain drug delivery." J. Drug Targ., 2001, 9, 23-37, abstract.

Aronson. Potassium channels in nervous tissue. Biochem. Pharmacol. 43(1):11-4 (Jan. 9, 1992) (abstract).

Bever. The current status of studies of aminopyridines in patients with multiple sclerosis. Ann. Neurol. 36 Suppl:S118-21 (1994) (abstract).

Pan et al. Polypeptide delivery across the blood-brain barrier. Curr. Drug. Targets CNS Nerol. Disord. 3(2):131-6 (Apr. 2004) (abstract).

Hayes et al. Pharmacokinetic studies of single and multiple oral doses of fampridine-SR (sustained release . . . Clin. Neuropharmacol. 26(4):185-92 (Jul.-Aug. 2003) (abstract).

\* cited by examiner

SEQUENCE LISTING

```
<160> NUMBER OF SEQ ID NOS: 1

<210> SEQ ID NO 1
<211> LENGTH: 12
<212> TYPE: PRT
<213> ORGANISM: Homo sapiens
<220> FEATURE:
<221> NAME/KEY: misc_feature
<223> OTHER INFORMATION: Membrane transporter peptide
<300> PUBLICATION INFORMATION:
<301> AUTHORS: Qing Lin et al.
<302> TITLE: Enhanced cell-permeant Cre protein for site-specific
      recombination in cultured cells
<303> JOURNAL: BMC Biotechnology
<304> VOLUME: 4
<305> ISSUE: 25
<306> PAGES: 1-13
<307> DATE: 2004-10-22

<400> SEQUENCE: 1
```

```
Ala Ala Val Leu Leu Pro Val Leu Leu Ala Ala Pro
1           5               10
```

4 AMINOPYRIDINE AND A PHARMACEUTICAL COMPOSITION FOR TREATMENT OF NEURONAL DISORDERS

CROSS-REFERENCE TO RELATED APPLICATIONS

This application is a continuation-in-part of U.S. patent application Ser. No. 11/023,241 filed Dec. 17, 2004, which is incorporated herein by reference.

FIELD OF THE INVENTION

The present invention relates to aminopyridine-conjugate compositions, methods of synthesizing such compositions and uses thereof. In particular, the invention relates to said aminopyridine-conjugate compositions and treatment of neurological disorders by administration thereof.

BACKGROUND OF THE INVENTION

Demyelinating neuropathies or diseases can occur in both the central nervous system and peripheral nervous system. Such conditions include the well-known disease multiple sclerosis as well as Guillain-Barré Syndrome, chronic demyelinating polyradiculoneuropathy, diabetic mellitus or the hereditary sensory-motor neuropathies such as Charcot-Marie-Tooth disease, Friedrich's ataxia, porphyria, lipoprotein neuropathies, and familial amyloid neuropathies. Demyelination of nerve fibers results in a short-circuiting of nerve impulses and thus a slowing or blocking of transmission along the nerve fibers with associated disabling symptoms including spasticity, loss of motor strength, and painful dysaesthesias.

A well-known problem in treatment of neurological disorders is ineffective delivery of therapeutic agents to neurons and associated cells due to the blood-brain and blood-nerve barriers. Considerable development has gone into the development of drugs and delivery systems for the transport of pharmacologically active species across the blood-brain or blood-nerve barrier. Such attempts have included derivatizing a pharmacologically active species to include specific moieties recognized by various membrane receptors or alternatively to add lipophilic moieties.

To date, while these approaches have shown promise, surprisingly little therapeutic progress has been made with respect to demyelinating conditions or diseases. Thus, there exists a need for compositions including therapeutic quantities of an active species wherein the compositions are capable of crossing the blood-brain barrier or blood-nerve barrier in a manner that inhibits side effects associated with such treatments.

SUMMARY OF THE INVENTION

A composition is provided having the formula:

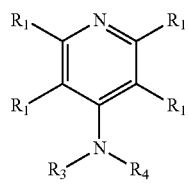

(I)

where $R_1$ in each occurrence is independently H or a $C_1$-$C_4$ hydrocarbon; $R_3$ is H, and $R_4$ is a moiety capable of crossing the blood brain barrier, termed a "transporter species" herein. The transporter species is selected from the group including an amino acid, a peptide, transferrin, gluconate, lactate, citrate, malate, fumarate, benzoate, salicylate, pyruvate and propionate.

In one embodiment $R_4$ is an amino acid such as alanine, asparagine, cysteine, glutamine, proline, serine, phenylalanine, tryptophan, leucine, methionine, isoleucine, tyrosine, histidine, valine, threonine, arginine, lysine, ornithine, gamma-aminobutyric acid, glycine, glutamic acid, or aspartic acid.

In a further embodiment, $R_4$ is a peptide such as a TAT peptide, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptide, or membrane transporter peptide (Ala-Ala-Val-Leu-Leu-Pro-Val-Leu-Leu-Ala-Ala-Pro (SEQ ID No. 1)).

In a further embodiment, an optional linker L is interposed between $R_4$ and the remainder of the compound. Additionally, the linker optionally has an alkyl backbone of less than eight carbon atoms and further optionally includes a pendent substituent such as a radioactive atom, a spectroscopically active marker, or an organic dye. The linker may be a terminal amino carboxylic acid such as gamma-aminobutyric acid.

Also provided by the present invention is an inventive aminopyridine conjugate having the formula

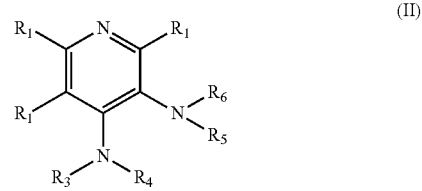

(II)

where $R_1$ in each occurrence is independently H or a $C_1$-$C_4$ hydrocarbon; $R_3$ and $R_5$ are H, and $R_4$ is H or a moiety capable of crossing the blood brain barrier and includes an amino acid, a peptide, transferrin, gluconate, lactate, citrate, malate, fumarate, benzoate, salicylate, pyruvate and propionate; and $R_6$ is H or a moiety capable of crossing the blood brain barrier and includes an amino acid, a peptide, transferrin, gluconate, lactate, citrate, malate, fumarate, benzoate, salicylate, pyruvate and propionate, wherein $R_4$ and $R_6$ are not both H.

Further provided are methods for making the compositions of the present invention.

DETAILED DESCRIPTION OF THE INVENTION

The present invention provides compositions for treating neuronal injuries, diseases, conditions, disorders and/or symptoms thereof by administering into a patient or subject having or suspected of having such neuronal injuries, diseases, conditions, disorders and/or symptoms thereof, a therapeutically effective amount of an inventive conjugate compound capable of traversing the blood brain barrier. In particular, the present invention provides compositions for treatment of neuronal injuries, diseases, conditions, disorders and/or symptoms involving demyelination.

Myelinated nerves have an insulating sheath of myelin that aids in conduction of electrical impulses along the axon. Loss of myelin, due to injury or disease, inhibits conduction of electrical impulses which are essential to nerve function, thus inhibiting nerve-mediated function. However, addition of a modulator of ion conductance or storage, such as a potassium channel blocker, aids in restoring normal nerve function.

Mono- and di-aminopyridines are known as modulators of ion uptake and release from cells, and may have other effects, such as stimulation of neurotransmitter release as well. For example, 4-aminopyridine has been characterized as an inhibitor of voltage-gated potassium channels as described, for example, in J. K. Aronson, Biochem. Pharmacol. 43: 11-14, 1992. However, these compounds have also been described as having effects on calcium uptake and/or storage, see for example, M. Grimaldi et al., J. Neurosci., 21:3135-3143, 2001.

The terms "patient" and "subject" as used herein mean all animals including humans. Examples of patients or subjects include humans, cows, dogs, cats, goats, sheep, and pigs.

Those skilled in the art are easily able to identify patients or subjects having a neuronal injury, disease, condition, disorder and/or a symptom thereof which involves demyelination. Illustrative examples of such injuries, diseases, conditions and disorders include: immune-related demyelinating disease such as Guillain-Barré syndrome, chronic immune demyelinating syndrome, multifocal motor neuropathy, anti-MAO syndrome, GALOP syndrome, anti-sulfatide antibody syndrome, anti-GM2 antibody syndrome, POEMS syndrome; toxin-related demyelination conditions such as those involving diphtheria, buckthorn, hexachlorophene, sodium cyanate, and tellurium; drug-related demyelination conditions such as those involving chloroquine, tacrolimus, perhexiline, procainamide, and zimeldine; hereditary conditions involving a demyelination component Charcot-Marie-Tooth disease, Friedrich's ataxia, porphyria, lipoprotein neuropathies, and familial amyloid neuropathies; acquired disorders involving a demyelination component such as multiple sclerosis, transverse myelitis and diabetes; and neurological injury involving a demyelination component, such as spinal cord injury or traumatic brain injury, and including diffuse axonal injury.

A therapeutically effective amount is an amount of an inventive composition that when administered to a patient or subject, ameliorates a symptom or sign of the demyelinating injury, disease, condition or disorder. In one embodiment, of particular interest in the context of the present invention are diseases and/or injuries involving symptoms or signs of demyelination, illustratively including spasticity, weakness, tremor, tingling, numbness, loss of balance, conduction block asthenia, ataxia, diplopia, dizziness, dysarthria, dysmetria, dysphagia, dysphonia, fatigability, hypotonia, nystagmus, oscillopsia, scanning speech, tremor, Babinski's sign, bladder dysfunction, clonus, fatigue, heat sensitivity, paralysis, Romberg's sign, spasticity, and trigeminal neuralgia.

The conjugate compounds of the present invention can be administered to a patient either alone or as part of a pharmaceutical composition. The inventive compounds and compositions are suitable for administration to patients by a variety of routes including intrathecally, intraventricularly, intravenously, orally, parenterally, and mucosally. In a preferred embodiment, the compositions are administered to patients either intrathecally or intraventricularly.

The inventive drug compositions are bioavailable to cells of the central nervous system as well as to cells of the peripheral nervous system. An inventive composition reduces symptoms and/or signs of a neurological disease or condition. In a particular embodiment, an inventive composition reduces symptoms and/or signs of demyelination.

It has been clearly demonstrated that mono- and di-aminopyridines have a therapeutic effect when administered to a patient or subject having a neurological condition. However, prior studies and drug compositions are limited in that their pharmacokinetic properties impose undesirable dosing conditions in order to achieve therapeutic levels, resulting in possible systemic side effects.

An inventive aminopyridine conjugate has the formula

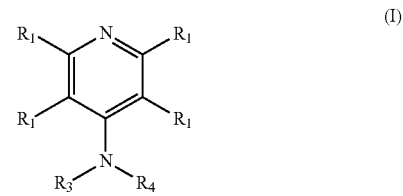

where $R_1$ in each occurrence is independently H or a $C_1$-$C_4$ hydrocarbon; $R_3$ is H, and $R_4$ is a moiety capable of crossing the blood brain barrier and includes an amino acid, a peptide, transferrin, gluconate, lactate, citrate, malate, fumarate, benzoate, salicylate, pyruvate and propionate. An amino acid included as a transport species $R_4$ is illustratively alanine, asparagine, cysteine, glutamine, proline, serine, phenylalanine, tryptophan, leucine, methionine, isoleucine, tyrosine, histidine, valine, threonine, arginine, lysine, ornithine, gamma-aminobutyric acid, glycine, glutamic acid, or aspartic acid. A peptide included as a transport species $R_4$ is illustratively a TAT peptide, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropin-releasing hormone, growth hormone-releasing hormone, luteinizing hormone, vasoactive intestinal peptide, or membrane transporter peptide.

In another embodiment, an inventive aminopyridine conjugate has the formula

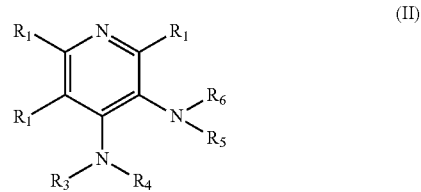

where $R_1$ in each occurrence is independently H or a $C_1$-$C_4$ hydrocarbon; $R_3$ and $R_5$ are H, and $R_4$ is H or a moiety capable of crossing the blood brain barrier and includes an amino acid, a peptide, transferrin, gluconate, lactate, citrate, malate, fumarate, benzoate, salicylate, pyruvate and propionate; and $R_6$ is H or a moiety capable of crossing the blood brain bather and includes an amino acid, a peptide, transferrin, gluconate, lactate, citrate, malate, fumarate, benzoate, salicylate, pyruvate and propionate, wherein $R_4$ and $R_6$ are not both H. An amino acid included as a transport species $R_4$ is illustratively alanine, asparagine, cysteine, glutamine, proline, serine, phenylalanine, tryptophan, leucine, methionine, isoleucine, tyrosine, histidine, valine, threonine, arginine, lysine, ornithine, gamma-aminobutyric acid, glycine, glutamic acid, or aspartic acid. A peptide included as a transport species $R_4$ and/or $R_6$ is illustratively a TAT peptide, bradykinin, beta-endorphin, bombesin, calcitonin, cholecystokinin, an enkephalin, dynorphin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptide, or membrane transporter peptide.

In a preferred embodiment, the monoaminopyridine is 4-aminopyridine. In another preferred embodiment, the diaminopyridine is 3,4-diaminopyridine.

According to the present invention, a mono- or di-aminopyridine conjugate composition as illustrated is formed by covalently bonding a first species which is a mono- or di-aminopyridine to a second species, the second species known to traverse the blood brain bather either by diffusion or by active or passive transport via a transmembrane transporter. In one embodiment, the second species includes a carboxyl moiety.

While the specific mechanism for the phenomenon is unclear, owing to the small molecular weight and lack of steric hindrance associated with a mono- or di-aminopyridine as illustrated above, inhibitory effects of the mono- or di-aminopyridine species on passage of the second or "transport species" across the blood brain barrier associated with conjugation of the two species are limited.

An inventive composition includes a second species or "transporter species" having the ability to pass the blood brain barrier when covalently bonded to a mono- or di-aminopyridine. In a preferred embodiment the transporter species is cleaved from the mono- or di-aminopyridine species to yield the mono- or di-aminopyridine species and the transporter species wherein the transporter species is itself is an active therapeutic or neurochemistry equilibrium modifier. The ability to deliver as a conjugate a mono- or di-aminopyridine with a second neuroactive species provides a previously unavailable ability to moderate a neurological therapeutic effect. As neuroactive compounds are subject to complex feedback mechanisms, the successful transport of a compound across the blood brain barrier has a moderated therapeutic effect owing to neurochemistry equilibrium shifts in response to the compound traversing the barrier. An inventive conjugate provides a mono- or di-aminopyridine that upon cleavage from the transporter species is in proximity to a neuroactive transport species that is an agonistic, antagonistic, or independently operating neuroactive species. The simultaneous dosage of a mono- or di-aminopyridine and the transporter species upon cleavage assures the desired dose is present. It is appreciated that two or more inventive conjugates are amenable to simultaneous delivery in order to provide still more refined therapeutic effects.

An inventive conjugate is preferably formed through an amide linkage between the first and second species.

In a preferred embodiment, a mono- or di-aminopyridine species is conjugated to a transporter species via a carbodiimide cross-linker. Carbodiimides are zero length cross-linkers that mediate the formation of an amide or phosphoramidate linkage between a carboxylate and an amine, or a phosphate and an amine, respectively. (Chu, B., Kramer, F. & Orgel, L. (1986), "Synthesis of an amplifiable reporter RNA for bioassays," Nucleic Acids Research, 14, 5591-5603. Hoare, D. & Koshland, D. E. (1966) J. Am. Chem. Soc., 88, 2057.) They react with carboxylic acids to form highly reactive O-acylisourea compounds that are very short lived but react with nucleophiles to form an amide bond. There are several competing and non-productive reactions, such as with water to regenerate the carboxylate group. This reaction works effectively between pH 4.5 and 7.5. Typical reaction times are 1.5-24 hours at 4-25° C. Molecules with a phosphate group such as the 5' phosphate on oligonucleotides can also react with amine-containing groups by using the carbodiimide reaction.

Optionally, a linker species is provided intermediate between the transporter moiety and the mono- or di-aminopyridine portion of an inventive conjugate. The linker in simplest form includes a carboxyl moiety and a moiety reactive with the transporter compound. Substituents extending from a linker are provided to modify the lipophilicity of an inventive conjugate, or tether a dye or spectroscopic marker. With the inclusion of a linker, care should be taken to limit both the molecular weight and the hydrophilicity of the linker in order to retain the ability to traverse the blood brain barrier. Transporter compound reactive moiety of the linker is dependent upon the transporter compound moiety to be bound thereto. Suitable chemistries for a variety of potential reaction moieties are found in *Comprehensive Organic Transformations*, R. C. Larock, John Wiley & Sons 1999.

It is appreciated that a linker, when present, is the preferred site for the attachment of an additional species. A substituent is optionally provided pendent from the linker backbone. The substituent illustratively includes a radioactive atom, a magnetic spectroscopically active marker and an organic dye. A radioactive atom is alternatively operative as a marker in isotope studies such as positron emission tomography, single photon emission computer tomography, radiological studies and the like. Common radio-isotopes used in medical imaging illustratively include $^{123}$I, $^{99m}$Tc, and other chelated radioisotopes as detailed in U.S. Pat. No. 6,241,963. Spectroscopically active markers include NMR/MRI active contrast enhancing moieties known to the art such as gadolinium, as detailed in "Contrast Agents 1: Magnetic Resonance Imaging" (Topics in Current Chemistry, 221) by Werner Krause, Springer Verlag, Berlin, Germany. Organic dyes, while recognized to have potentially distinct NMR/MRI signatures, are provided to yield an optically active spectroscopic signature suitable for biopsy, surgical identification, or preclinical studies of tissue treated by an inventive compound.

In an alternative embodiment, a mono- or di-aminopyridine is conjugated to a transporter species in the form of an ester or acid chloride. Preferably a mono- or di-aminopyridine is reacted with a transporter species ester. It is appreciated that an amine protecting group is needed to protect one amine group of 3,4-aminopyridine during a coupling reaction to a transport species.

A protecting group for the amino function can be an acyl group, such as an acyl of an aliphatic, aromatic or araliphatic carboxylic acid, especially lower alkanoyl such as acetyl or propionyl, or aroyl such as benzoyl, or formyl or an acyl of a carbonic acid half-ester, such as benzyloxycarbonyl or fluorenylmethyloxycarbonyl (Fmoc). Examples of amino-protecting groups illustratively include the formyl ("For") group, the trityl group, the phthalimido group, the trichloroacetyl group, the trifluoroacetyl group, the chloroacetyl, bromoacetyl, and iodoacetyl groups, urethane-type protecting groups, such as t-butoxycarbonyl ("t-Boc"), 2-(4-biphenylyl) propyl-2-oxycarbonyl ("Bpoc"), 2-phenylpropyl-2-oxycarbonyl ("Poe"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluyl)propyl-2-oxycarbonyl, cyclopentanyloxycarbonyl, 1-methylcyclopentanyloxycarbonyl, cyclohexanyloxycarbonyl, 1-methyl-cyclohexanyloxycarbonyl, 2-methylcyclohexanyl-oxycarbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("Fmoc"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyl-oxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxycarbonyl, α-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl and the like; the benzoylmethylsulfonyl group, the 2,2,5,7,8-pentamethylchroman-6-sulfonyl group ("PMC"), the dithiasuccinoyl ("Dts") group, the 2-(nitro)phenyl-sulfenyl group ("Nps"), the diphenylphosphine oxide group, and like amino-protecting groups. The species of amino-protecting group employed is not critical so long as the derivatized amino group is stable to the conditions of the subsequent reaction(s) and can be removed at the appropriate point without disrupting the remainder of the molecule. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," $2^{nd}$ ed., John Wiley and Sons, New York, N.Y., 1991, Chapter 7; M. Bodansky, "Principles of Peptide Synthesis," $1^{st}$ and $2^{nd}$ revised Ed., Springer-Verlag, New York, N.Y., 1984 and 1993; and J. M. Stewart and J. D. Young, "Solid Phase Peptide Synthesis," $2^{nd}$ Ed., Pierce Chemical Co., Rockford, Ill., 1984; E. Atherton and R. C. Shephard, "Solid Phase Peptide Synthesis—A Practical Approach" IRL Press, Oxford, England (1989).

The cleavage of such an acyl residue serving as protecting group from an amino function can be performed by known methods, such as solvolysis exemplified by alcoholysis. Moreover it can be brought about by hydrolysis in acidic or basic medium. The alcoholytic cleavage of an acyl residue can be effected, such as in presence of a basic reagent and/or at elevated temperature, e.g. from 50° C. to 120° C. with a lower alkanol such as n-butanol or ethanol. A base is used such as an alkali metal alcoholate, such as sodium or potassium ethoxide or an alkali metal hydroxide, such as sodium or potassium hydroxide.

Other aminoprotecting groups, such as lower alkoxy-carbonyl-groups e.g. t-butoxycarbonyl, are cleaved under mild acidic conditions, such as by treatment with trifluoroacetic acid. Another group, cleavable under especially mild conditions is an ethoxycarbonyl group carrying in the β-position a silyl group substituted with three hydrocarbon residues, such as triphenylsilyl, dimethyl-butylsilyl or especially trimethylsilyl. These are cleaved by reaction with fluoride ions, especially fluoride salts of quaternary ammonium bases, such as tetraethylammonium fluoride.

Compositions suitable for administration optionally include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, saline, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

Inventive compositions optionally contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

An inventive compound is also delivered in conjunction with an active therapeutic compound. The therapeutic compound illustratively being active as antibiotic, a gamma or beta radiation emitting species, an anti-inflammatory, an anti-tumoral, an antibody, a hormone, an enzyme, and an antigenic peptide or protein.

The complex conjugates of the present invention can be administered to a patient at dosage levels in the range of about 5 mg to about 1500 mg per day of an inventive composition. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

As stated above, intrathecal, intravenous, intramuscular, and intraventricular administration of inventive complex conjugates is operative. Examples of well-known implants and modules useful in the present invention for intrathecal or intraventricular administration include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

The following examples are presented below to illustrate particular embodiments of the invention and are not intended to limit the scope of the specification, including the claims, in any way.

EXAMPLE 1

Preparation of glutamyl-4-aminopyridine conjugate

A mixture of 4-aminopyridine (5 mmol) and glutamic acid (5 mmol) is added to 0.1M carbodiimide [N-ethyl-N'-(3-dimethylaminopropyl) carbodiimide or EDC] in distilled water adjusted to pH 4.5, such that the final volume is 200 ml. The reaction is performed for 24 hours at 4° C. The resulting glutamyl-4-aminopyridine conjugate is collected as an oil and purified to pharmaceutical purity.

EXAMPLE 2

Preparation of lactyl-4-aminopyridine

A mixture of 4-aminopyridine (5 mmol) and lactyl acetate (5 mmol) is added to 0.1M carbodiimide [N-cyclohexyl-N'-2-(4-methyl-morpholinium) ethyl carbodiimide-p-toluene sulphonate or CMC] in distilled water adjusted to pH 4.5, such that the final volume is 200 ml. The reaction is performed for 24 hours at 4° C. The resulting lactyl-4-aminopyridine is collected as an oil and purified to pharmaceutical purity.

Any patents or publications mentioned in this specification are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The apparatus and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A compound having the formula

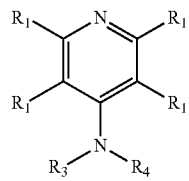

where $R_1$ in each occurrence is independently H or a $C_1$-$C_4$ hydrocarbon; $R_3$ is H, and $R_4$ is a glutaminyl.

2. A therapeutic composition comprising the compound of claim 1 in a physiologically suitable solvent for administration by a route selected from the group consisting of: parenteral, intraventricular, and intrathecal.

3. The composition of claim 2 further comprising an adjuvant.

* * * * *